US00PP13185P2

(12) United States Plant Patent
Utecht

(10) Patent No.: US PP13,185 P2
(45) Date of Patent: Nov. 5, 2002

(54) GERANIUM PLANT NAMED 'FISDAPI'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/989,122

(22) Filed: Nov. 21, 2001

(65) Prior Publication Data

US 2002/0088037 P1 Jul. 4, 2002

(51) Int. Cl.[7] ..... A01H 5/00

(52) U.S. Cl. ..... Plt./329

(58) Field of Search ..... Plt./329

*Primary Examiner*—Kent L. Bell
(74) *Attorney, Agent, or Firm*—Foley & Lardner

(57) ABSTRACT

A new and distinct cultivar of geranium plant named 'Fisdapi', as described and illustrated, and particularly characterized by the combined features of large, round, pink and purple, bi-colored flowers, relatively large and wide inflorescences, dark-green foliage, and medium sized, uniform plant habit.

1 Drawing Sheet

BOTANICAL CLASSIFICATION

*Pelargonium zonale.*

VARIETY DENOMINATION

'Fisdapi'.

BACKGROUND OF THE INVENTION

The present invention comprises a new and distinct cultivar of geranium, botanically known as *Pelargonium zonale,* and hereinafter referred to by the cultivar name 'Fisdapi'.

'Fisdapi' is a product of a planned breeding program which had the objective of creating new geranium varieties with bi-colored flowers in combination with dark-green foliage.

'Fisdapi' originated from a hybridization made by the inventor Angelika Utecht in a controlled breeding program in Galdar, Gran Canaria, Spain, in 1995. The female parent is an unpatented hybrid seedling, no. K93-859-4, which was derived from a cross of the unpatented variety 'Flofiti' and the variety 'Feeling' (U.S. Plant Pat. No. 6,717).

'Flofiti' is characterized by pink flowers with darker eyes, large umbels, uniform, dark-green foliage, and moderately compact plant habit. 'Feeling' has large pink flowers with macules, and large umbels, medium green foliage with weak zonation, and more moderately compact plant habit and well-branched.

The male parent of 'Fisdapi' is the patented cultivar 'Fisbravo', (U.S. Plant Pat. No. 9,765), characterized by pink colored flowers with large purple eyes, dark-green, slightly zoned foliage and moderately compact plant habit.

'Fisdapi' was selected as one flowering plant within the progeny of the stated cross by Angelika Utecht in 1996 in a controlled environment in Galdar, Gran Canaria, Spain.

The first act of asexual reproduction of 'Fisdapi' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fisdapi' are firmly fixed and are retained through successive generations of asexual reproduction. The new cultivar reproduces true to type.

'Fisdapi' has not been observed under all possible environmental conditions. The phenotype may vary significantly with variations in environment such as temperature, light intensity and day length.

The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisdapi' which in combination distinguish this geranium as a new and distinct cultivar:

1. Round, dark-pink flowers with large purple eyes;
2. Wide umbels on long peduncles;
3. Dark-green foliage, usually without zonation;
4. Moderately compact growth, and medium sized, round plant habit; and
5. Mid season spring flowering response.

Of the many commercial cultivars known to the present inventor, the closest comparison to 'Fisdapi' is the parental cultivar 'Fisbravo'.

In comparison to 'Fisbravo', 'Fisdapi' has flowers of similar shape and size, and with a similar markings, but the general flower color is much deeper and more intense. Umbels of 'Fisdapi' are somewhat larger, rounder in shape and are consist of a higher number of flowers.

In comparison to K93-859-4, the female parental cultivar, has similar flower color: bluish-pink flowers with dark pink eyes, medium sized umbels, significantly lighter green foliage with weak zonation, and a compact, low plant habit.

BRIEF DESCRIPTION OF THE DRAWINGS

The accompanying photographic drawing shows typical flower and foliage characteristics of 'Fisdapi' with colors being as true as possible with an illustration of this type. The plants were grown in 8 inch containers and had not been pinched.

DETAILED BOTANICAL DESCRIPTION

In the following description color references are made to The Royal Horticultural Society Colour Chart (R.H.S.). The color values were determined indoors from plants developed in a green-house in May, 2000 in Hillscheid, Germany. The measurements were taken in Langley in early July, 2001, 18 weeks after planting of rooted cuttings.

Inflorescence:
- *Type*.—Umbel.
- *Shape*.—Semi-spherical to umbrella-shape.
- *Average diameter*.—134 mm.
- *Average depth*.—76 mm.
- *Peduncle length*.—228 mm.
- *Peduncle color*.—Mostly green, RHS 143 B, in parts slightly brownish RHS 173 A.
- *Pedicel length*.—34 mm, occasionally with spur (rare for a zonale variety).
- *Pedicel color*.—Base green, RHS 144 A,middle brownish 179 A, near upper end dark brown-red, RHS 184 A.
- *Number of flowers per umbel*.—Average 20 to 25.

Corolla:
- *Average diameter*.—52 mm.
- *Form*.—Semi-double.
- *Shape*.—Round.
- *Number of petals*.—Average 7.4.
- *Number of petaloids*.—Average 0–1.
- *Shape of petals*.—Obovate, base acute, upper end is truncate or rounded, margins are entire, occasionally slightly serrulated at the tips.
- *Size of petals*.—Upper petals: 26–28 mm long, 19–24 mm wide (somewhat variable); lower petals: 24–26 mm long, 23–25 mm wide.
- *Color (general tonality from a distance of three meters)*.—Bluish pink, with large brilliant red eyes.
- *Color of upper petals*.—Near margin RHS 66 C.
- *Markings of upper petals*.—Large red macules, between RHS 52 A and RHS 57 A, white bases, RHS 155 D, distinct purple veins RHS 74 C.
- *Color of lower petals*.—Somewhat variable from RHS 66 C to RHS 68 A.
- *Markings of lower petals*.—Red macules, RHS 57 B, and light pink bases, from approximately RHS 68 C to RHS 68 D.
- *Color of lower surface of petals*.—Mainly RHS 73 A, towards the bases lighter RHS 73 C, and reddish veins, RHS 74 C.
- *Petaloid shape*.—Irregular.
- *Petaloid color*.—Upper surface is RHS 66 C, Lower surface is RHS 73 A.
- *Color of sepals*.—Outer surface: base dark brown, RHS 181 A, tips light green RHS 143 B to RHS 143 C; inner surface: base RHS 179 A, tips RHS 143 C.
- *Number of sepals*.—5.
- *Shape of sepals*.—Linear to lanceolate, acute tip, truncate base, surface with weak, very short pubescence, margin entire.
- *Size of sepals*.—10–11 mm long, 4 mm wide for the largest upper sepal, 2–3 mm in width for the other sepals.

Bud: (just before petals unfold):
- *Shape*.—Narrow elliptical.
- *Color (lower part, sepals)*.—Green, RHS 143 B.
- *Color (upper part, petals)*.—Purple-pink, somewhat variable from RHS 66 C to RHS 66 D.
- *Length*.—18–20 mm.
- *Width*.—9 mm.

Reproductive organs:
- *Androecium*.—7 fertile anthers, filaments white, RHS 155 D, to light pink, RHS 66 D, plenty of pollen production, orange, RHS 30 A.
- *Gynoecium*.—One pistil per plant, red style and stigma, RHS 57 A, 5 to 6-lobed stigma.
- *Fertility/seed set*.—No seed observed.

Spring flowering response period: In Hillscheid, Germany, in 2000 plants had on average 1.3 flowers open 9 weeks after planting of rooted cuttings.

Outdoor flower production: Continuously flowering, the flower count in 2000 in Hillscheid, Germany, indicated on average 3 inflorescences per plant in mid May.

Durability: Good stability of flower color; relatively good rain resistance.

Lastingness of the individual flower: About 8–9 days at 18° C., about 18 days for the umbel.

Fragrance: None.

Pest/disease resistance/susceptibility: No observations to date.

PLANT

Foliage:
- *Shape*.—Kidney-shaped, with relatively distinct lobes, with open to wide open, cordate base.
- *Margin*.—Bicrenated, distinctly wavy.
- *Texture*.—Upper surface smooth, velvety.
- *Size of leaf*.—98.5 mm wide, 62.5 mm long.
- *Color of upper surface*.—Dark-green, approximately RHS 137 A to RHS 137 B.
- *Zonation*.—Usually absent, only very weak on young leaves: darker green color, about RHS 147 A.
- *Color of lower surface*.—RHS 137 D.
- *Petioles*.—60–70 mm long, 3–4 mm in diameter, light to medium-green, RHS 137 D.

General appearance and form:
- *Stem color*.—Green, RHS 137 D.
- *Internode length*.—10–30 mm.
- *Branching pattern*.—8.0 branches.
- *Size of plants*.—Height of foliage canopy 28 cm, width/diameter: 42.6 cm measured from the top of the soil (base of the main stem) to the foliage upper surface, without inflorescences.

I claim:

1. A new and distinct cultivar of geranium plant named 'Fisdapi', as described and illustrated herein.

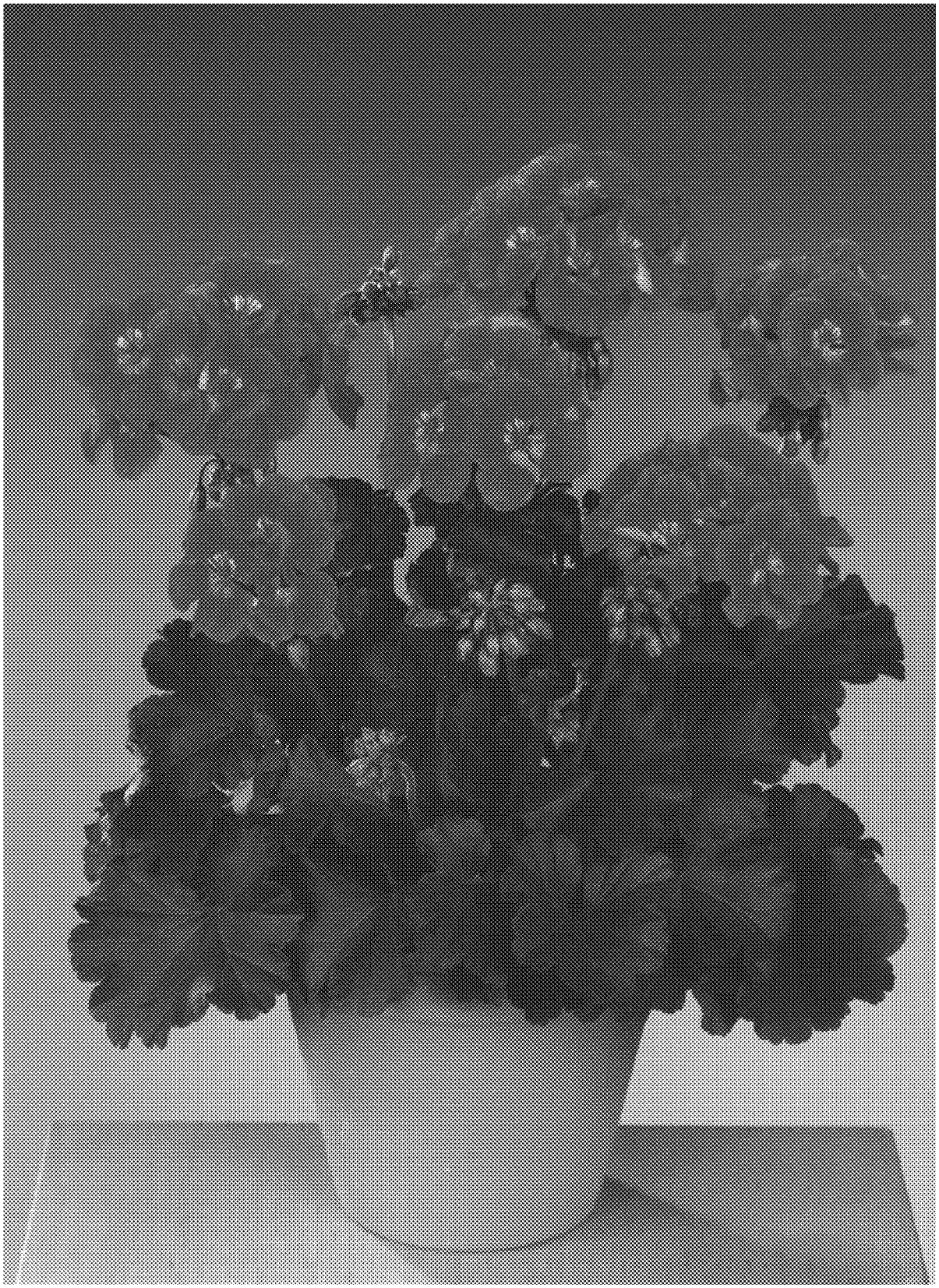

* * * * *